(12) United States Patent
Takimoto et al.

(10) Patent No.: US 8,237,848 B2
(45) Date of Patent: Aug. 7, 2012

(54) IMAGE SENSING APPARATUS AND METHOD FOR SENSING TARGET THAT HAS A DEFECTIVE PORTION REGION

(75) Inventors: Masafumi Takimoto, Kawasaki (JP); Yusuke Mitarai, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 284 days.

(21) Appl. No.: 12/649,079

(22) Filed: Dec. 29, 2009

(65) Prior Publication Data

US 2010/0171852 A1 Jul. 8, 2010

Related U.S. Application Data

(63) Continuation of application No. PCT/JP2008/059888, filed on May 29, 2008.

(30) Foreign Application Priority Data

Jun. 29, 2007 (JP) .................................. 2007-172749

(51) Int. Cl.
*H04N 5/217* (2011.01)
(52) U.S. Cl. ......... 348/345; 348/125; 348/128; 348/354
(58) Field of Classification Search .......................... None
See application file for complete search history.

(56) References Cited

U.S. PATENT DOCUMENTS

| | | | | |
|---|---|---|---|---|
| 5,311,598 A * | 5/1994 | Bose et al. | ..................... | 382/149 |
| 5,353,357 A * | 10/1994 | Longest et al. | ............... | 382/141 |
| 5,845,002 A * | 12/1998 | Heck et al. | ..................... | 382/110 |
| 6,396,949 B1 * | 5/2002 | Nichani | ......................... | 382/173 |
| 8,008,641 B2 * | 8/2011 | Harris et al. | ............. | 250/559.41 |
| 2002/0191831 A1 * | 12/2002 | Spoto et al. | ................... | 382/141 |
| 2003/0169364 A1 * | 9/2003 | Watanabe et al. | ............. | 348/345 |
| 2004/0105001 A1 * | 6/2004 | Chang et al. | .................... | 348/92 |
| 2005/0099523 A1 * | 5/2005 | Konishi et al. | ................ | 348/345 |
| 2006/0171699 A1 * | 8/2006 | Nakai et al. | ..................... | 396/125 |
| 2007/0285557 A1 * | 12/2007 | Wu | .............................. | 348/345 |
| 2010/0295986 A1 * | 11/2010 | Hori | .............................. | 348/354 |

FOREIGN PATENT DOCUMENTS

| | | |
|---|---|---|
| JP | 08-285557 A | 11/1996 |
| JP | H11-281585 | 10/1999 |
| JP | 2001-185591 | 7/2001 |
| JP | 2001-202496 | 7/2001 |
| JP | 03601031 | 12/2004 |

OTHER PUBLICATIONS

Coulthard, M.A.; "Image Processing for Automatic Surface Defect Detection," Image Processing and Its Applications, 3rd.; Jul. 18, 1989, p. 192-196.*

"A Method of Industrial Parts Surface Inspection Based on an Optics Model" Norifumi Katafuchi et al., Jul. 25, 1997.

* cited by examiner

*Primary Examiner* — David Ometz
*Assistant Examiner* — Dwight C Tejano
(74) *Attorney, Agent, or Firm* — Fitzpatrick, Cella, Harper & Scinto

(57) ABSTRACT

This invention is directed to easily set the image sensing conditions of an image sensing apparatus. The image sensing apparatus includes a first control means for controlling to change the image sensing conditions, an image sensing means to sense an image sensing target at every first time interval, and to calculate the evaluation value of the sensed image, and a second control means for controlling to change the image sensing conditions within the range where the evaluation value obtained by the first control means changes from increase to decrease, the image sensing means to sense the image sensing target at every second time interval smaller than the first time interval, and to calculate the evaluation value of the sensed image.

16 Claims, 8 Drawing Sheets

IMAGE SENSING APPARATUS AND METHOD FOR SENSING TARGET THAT HAS A DEFECTIVE PORTION REGION

CROSS-REFERENCE TO RELATED PATENT APPLICATIONS

This application is a continuation of co-pending Application No. PCT/JP2008/059888, filed May 29, 2008, which is incorporated by reference herein in its entirety, as if fully set forth herein, and claims the benefit of priority under 35 U.S.C. §119, based on Japanese Priority Application No. JP 2007-172749, filed Jun. 29, 2007, which is incorporated by reference herein in its entirety, as if fully set forth herein.

TECHNICAL FIELD

The present invention relates to an image sensing apparatus and method for setting image sensing conditions when sensing an image.

BACKGROUND ART

At the production site of industrial products, the manufacture of defectives is prevented by inspecting whether a target component is non-defective. The inspection of a target component is executed not only in the final manufacturing process of a product but also during the manufacture.

Some inspection processes require high inspection accuracies, but some do not. Inspections vary from one using an inspection apparatus to one based on human subjective evaluation. Compared to a mechanical inspection, an inspection based on human subjective evaluation readily generates an individual difference in inspection. A typical subjective evaluation is a visual inspection by human visual observation. In visual inspection of industrial products, various kinds of features are detected, including the shape and density of a defect. For example, the shapes and sizes of defects such as color inconsistency, stain, and scratch generally handled in visual inspection are not defined, and it is hard to detect such defects. To efficiently perform a visual inspection, demand has arisen for a visual inspection automated by a visual inspection apparatus.

Patent reference 1 discloses a technique of rotating an object to be sensed, changing illumination conditions, and sensing many images. However, it is difficult to detect conditions suitable for a visual inspection from various image sensing conditions. This requests a complicated operation of a user.

Patent Reference 1: Japanese Patent Registration No. 03601031

DISCLOSURE OF INVENTION

Problems that the Invention is to Solve

It is an object of the present invention to easily set the image sensing conditions of an image sensing apparatus. It is another object of the present invention to increase the setting accuracy of the image sensing conditions of an image sensing apparatus.

Means of Solving the Problems

To achieve the above objects, according to an invention of claim 1, an image sensing apparatus comprises image sensing means for sensing an image sensing target to acquire a sensed image, illumination means for illuminating the image sensing target in image sensing by the image sensing means, image sensing condition change means for changing an image sensing condition when sensing the image sensing target, calculation means for calculating, as an evaluation value, information on a contrast of the sensed image acquired by the image sensing means, first control means for controlling the image sensing condition change means to change the image sensing condition, the image sensing means to sense the image sensing target at every first time interval, and the calculation means to calculate an evaluation value of the sensed image, second control means for controlling the image sensing condition change means to change the image sensing condition within a range where the evaluation value obtained by the first control means changes from increase to decrease, the image sensing means to sense the image sensing target at every second time interval smaller than the first time interval, and the calculation means to calculate an evaluation value of the sensed image, and image sensing condition setting means for setting the image sensing condition based on the evaluation value obtained by the second control means.

According to an invention of claim 6, an image sensing apparatus comprises image sensing means for sensing an image sensing target to acquire a sensed image, enhancement processing means for enhancing a defective portion region on the sensed image acquired by the image sensing means in accordance with a surface structure of the image sensing target, and image sensing condition setting means for setting an image sensing condition of the image sensing means based on the sensed image in which the defective portion region is enhanced.

According to an invention of claim 11, an image sensing apparatus comprises image sensing means for sensing an image sensing target to acquire a sensed image, illumination means for illuminating the image sensing target in image sensing by the image sensing means, image sensing condition change means for changing an image sensing condition when sensing the image sensing target, enhancement processing means for enhancing a defective portion region on the sensed image in accordance with a surface structure of the image sensing target, calculation means for calculating an evaluation value as information on a contrast of the sensed image in which the defective portion region is enhanced, first control means for controlling the image sensing condition change means to change the image sensing condition, the image sensing means to sense the image sensing target at every first time interval, and the calculation means to calculate an evaluation value of the sensed image, second control means for controlling the image sensing condition change means to change the image sensing condition within a range where the evaluation value obtained by the first control means changes from increase to decrease, the image sensing means to sense the image sensing target at every second time interval smaller than the first time interval, and the calculation means to calculate an evaluation value of the sensed image, and image sensing condition setting means for setting the image sensing condition based on the evaluation value obtained by the second control means.

Effects of the Invention

The present invention can easily set the image sensing conditions of an image sensing apparatus. Also, the present invention can increase the setting accuracy of the image sensing conditions of an image sensing apparatus.

Other features and advantages of the present invention will become apparent from the following description of exem-

BRIEF DESCRIPTION OF DRAWINGS

The accompanying drawings, which are incorporated in and constitute a part of the specification, illustrate embodiments of the invention and, together with the description, serve to explain the principles of the invention.

Figure 1:
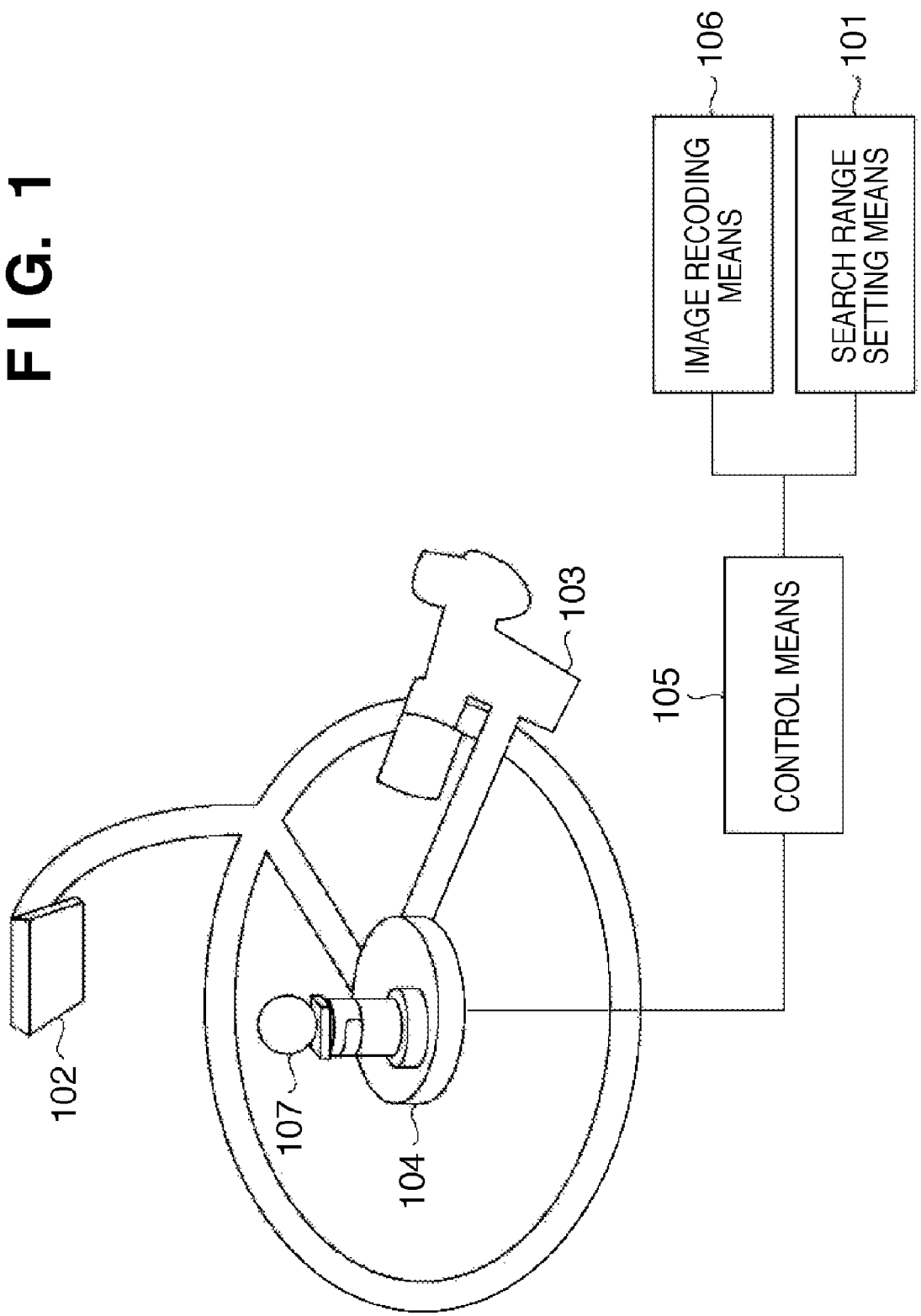
FIG. 1 is a view showing the arrangement of a visual inspection apparatus according to the first embodiment.

| DESCRIPTION OF THE REFERENCE NUMERALS | |
|---|---|
| 101 | search range acquisition means |
| 102 | illumination means |
| 103 | image sensing means |
| 104 | driving means |
| 105 | control means |
| 106 | image recoding means |
| 107 | image sensing target |

BEST MODE FOR CARRYING OUT THE INVENTION

First Embodiment

The first embodiment will be described in detail below.

FIG. 1 is a view showing the arrangement of a visual inspection apparatus according to the embodiment. The visual inspection apparatus is an inspection apparatus which senses an object to be inspected that is irradiated with illumination light, and inspects it from the sensed image. To sense an object to be inspected, the visual inspection apparatus generally includes an image sensing means.

A search range acquisition means 101 includes an input device such as a keyboard or mouse, and a display device such as a monitor. The search range acquisition means 101 acquires data within the search range of an object to be inspected. The user observes the object displayed on the display device, and inputs a search range with the input device. The search range is a region to be inspected when performing a visual inspection.

An illumination means 102 includes a luminaire using a fluorescent light, halogen lamp, slit-shaped light, area light, LED, prism, or the like. The illumination means 102 emits illumination light to enhance the contrast of an object to be inspected.

An image sensing means 103 senses an object to be inspected that is irradiated with illumination light emitted by the illumination means 102, acquiring the image of the object. The image sensing means 103 includes an optical means such as a video camera or infrared sensor.

A driving means 104 includes a motor and driving gear. The motor operates to transfer the driving force to the illumination means 102 and image sensing means 103 via the driving gear, changing the positions of the illumination means 102 and image sensing means 103.

A control means 105 includes a CPU and RAM. The RAM stores a control program for controlling the visual inspection apparatus. The CPU reads the control program from the RAM and executes processing based on the control program to control each building component of the visual inspection apparatus. The control program includes a driving program for driving the driving means 104, illumination means 102, and image sensing means 103, and an information processing program for processing data in the search range that is transmitted from the search range acquisition means 101.

An image recoding means 106 includes a recording means such as a hard disk, and records an image acquired by the image sensing means 103. The image acquired by the image sensing means 103 is transmitted to the image recoding means 106 via the control means 105.

An image sensing target 107 undergoes a visual inspection, and includes some assemblies or the like. The image sensing target 107 in the embodiment has a defective portion region. The defective portion is a scratch, dirt, or the like on the image sensing target 107 and is to be detected in visual inspection.

To enhance the contrast between the defective portion region and the remaining region, the image sensing target 107 is irradiated with illumination light emitted by the illumination means 102 and sensed by the image sensing means 103.

Processing in the embodiment using the visual inspection apparatus in FIG. 1 will be explained.

Figure 2:
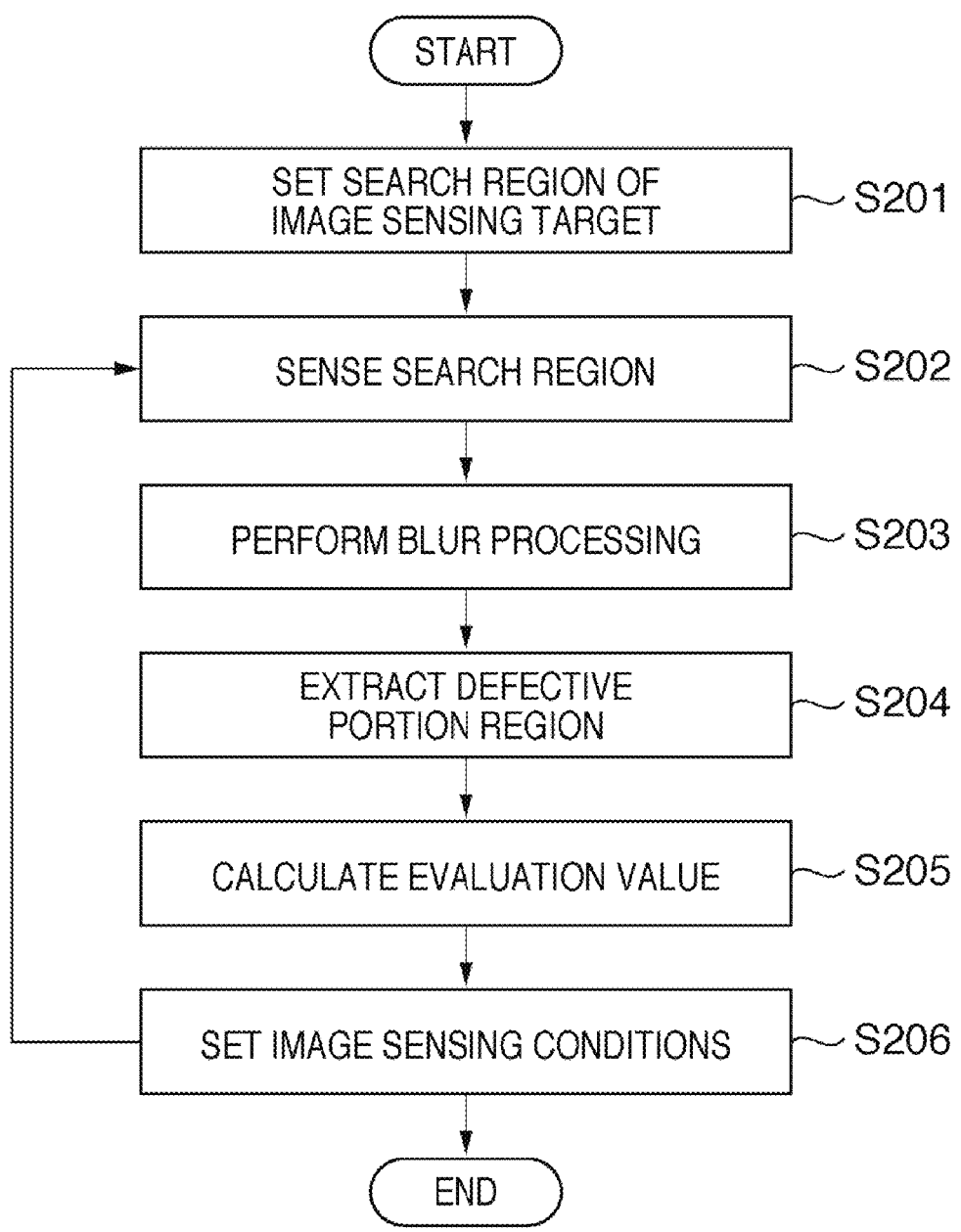
FIG. 2 is a flowchart showing the sequence of visual inspection processing according to the first embodiment.

FIG. 2 shows the sequence of visual inspection processing in the embodiment using the visual inspection apparatus in FIG. 1. In FIG. 2, processing to detect a defective portion of the image sensing target 107 is performed as an example of visual inspection.

(Step 201) In step 201, an image sensing means 103 senses the image sensing target 107 to set the search region of the image sensing target. The search region is a region to be inspected when performing a visual inspection. The image sensing means 103 senses the image sensing target 107 from a plurality of image sensing directions, acquiring a plurality of images of the image sensing target 107. The display device such as a monitor displays the acquired images, and the search region is set based on a user instruction.

Figure 3:
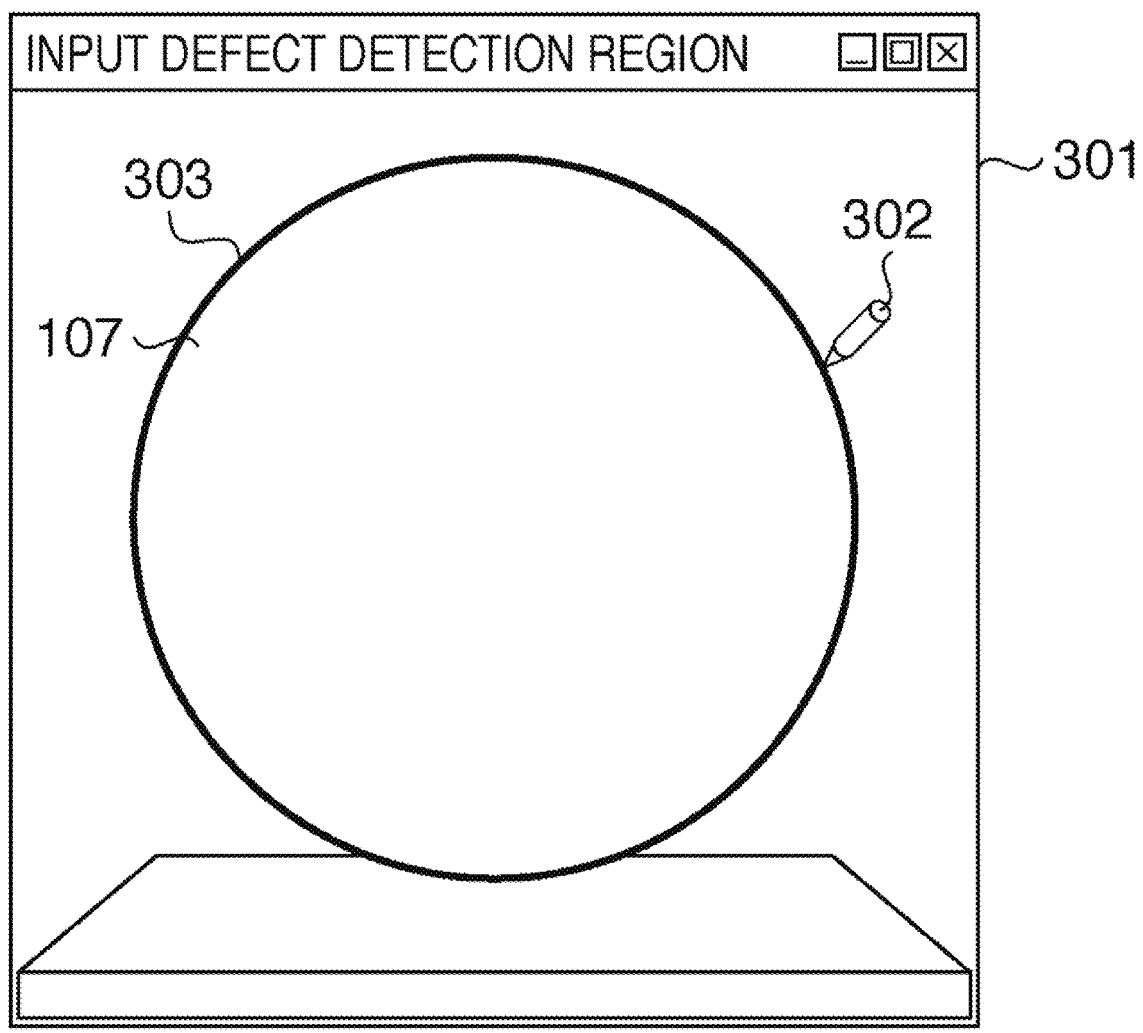
FIG. 3 is a view showing a UI (User Interface) for setting a search region in the first embodiment.

FIG. 3 is a view showing a UI (User Interface) for setting a search region. A target image shown in FIG. 3 is an image sensed by the image sensing means 201.

A UI 301 is used to set a search region by a user who executes a visual inspection.

The image sensing target 107 undergoes a visual inspection.

A pointer 302 is used to set the search region of the image sensing target 107 based on a user instruction.

A search region 303 is the search region of the image sensing target 107 designated with the pointer 302.

With an indicating device such as a mouse or touch pen, the user operates the pointer 302 on the UI 301 to designate the search region 303 of the image sensing target 107. The search range acquisition means 101 acquires data in the designated search region 303.

However, when the search region 303 is set based on a user instruction, the user may not be able to designate an optimal search region if his skill is poor. In such a case, the search region 303 designated by the user may be reconfigured to set a new search region 303. As the reconfiguration method, for example, a change of the luminance value or color information (e.g., R, G, and B values) is used. According to this method, a point which forms the boundary of the designated search region 303 is extracted. A change of the luminance value or color information in a region near the extracted point is calculated. If there is a point in the neighboring region at which the change amount of the luminance value or color information is larger than that at the point which forms the boundary of the search region 303, the point exhibiting the larger change amount is set as a point which forms the boundary of the search region 303. This processing is executed for each point which forms the boundary of the search region 303, thereby reconfiguring the boundary of the search region 303.

When the image sensing means 103 moves, the relative positions of the image sensing means 103 and image sensing target 107 sometimes change. The changed relative positions change the search region 303 on the image of the image sensing target 107. Even if the search region 303 changes, an appropriate search region 303 can be set using the method of reconfiguring the search region 303.

By using an infrared ray, stereo computer vision technique, or the like, 3D information of the periphery of the image sensing target 107 may be acquired. The relative positions of the image sensing target 107 and image sensing means 103 are calculated from the 3D information and used to reconfigure the search region 303.

(Step 202) In step 202, the control means 105 functions as an image sensing condition change means. While the control means 105 changes image sensing conditions, the image sensing means 103 senses the search region 303 of the image sensing target 107. The image sensing conditions are the positions and orientations of the image sensing means 103 and illumination means 102, the illumination intensity of the illumination means 102, and the like. When changing the image sensing conditions, the driving means 104 receives a control instruction from the control means 105 and changes the positions and orientations of the image sensing means 103 and illumination means 102. In accordance with a control instruction from the control means 105, the illumination means 102 changes the illumination intensity. While the image sensing conditions change, the image sensing means 103 senses the image sensing target 107 at every preset timing. The number of images to be sensed may be set in advance based on a user instruction. When the number of images is set, the timing at which the set number of images can be sensed is calculated from the driving speeds of the image sensing means 103 and illumination means 102. By this processing, a plurality of images can be acquired under various image sensing conditions.

(Step 203) In step 203, the control means 105 functions as an enhancement processing means for enhancing a defective portion region on the sensed image, and executes blur processing for the image acquired in step 202. The blur processing is to remove a texture pattern appearing on the surface of an image sensing target and enhance a defective portion region on the sensed image. In the embodiment, the blur processing means image frequency reduction processing such as averaging processing or filter processing. The texture pattern arises from a surface structure such as the material or surface shape of an image sensing target, and appears almost regularly on the surface of the image sensing target. When a defective portion such as a scratch is extracted in visual inspection, the texture pattern is sometimes erroneously detected as a defective portion. To prevent this, the texture pattern is removed from the image of the image sensing target 107 by blur processing to enhance a defective portion region on the sensed image and improve the detection accuracy of the defective portion.

Figure 4:
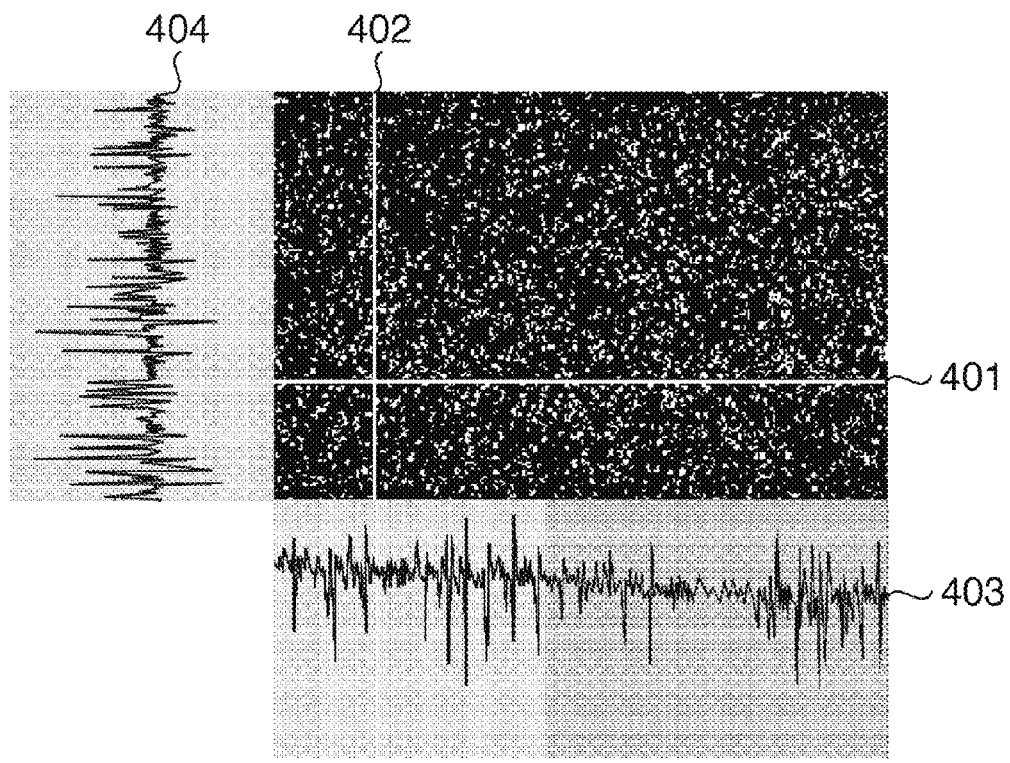
FIG. 4 is a view exemplifying a texture pattern appearing on the surface of an image sensing target.

FIG. 4 is a view exemplifying a texture pattern generated by granular projections appearing on the surface of the image sensing target 107.

FIG. 4 shows the surface of the image sensing target 107 when the image sensing target 107 is coated with a synthetic resin. As shown in FIG. 4, small mottles appear. The mottle represents a projection. In FIG. 4, lines 401 and 402 are set, and luminance values on the respective lines are extracted, obtaining luminance distributions 403 and 404.

Figure 5:
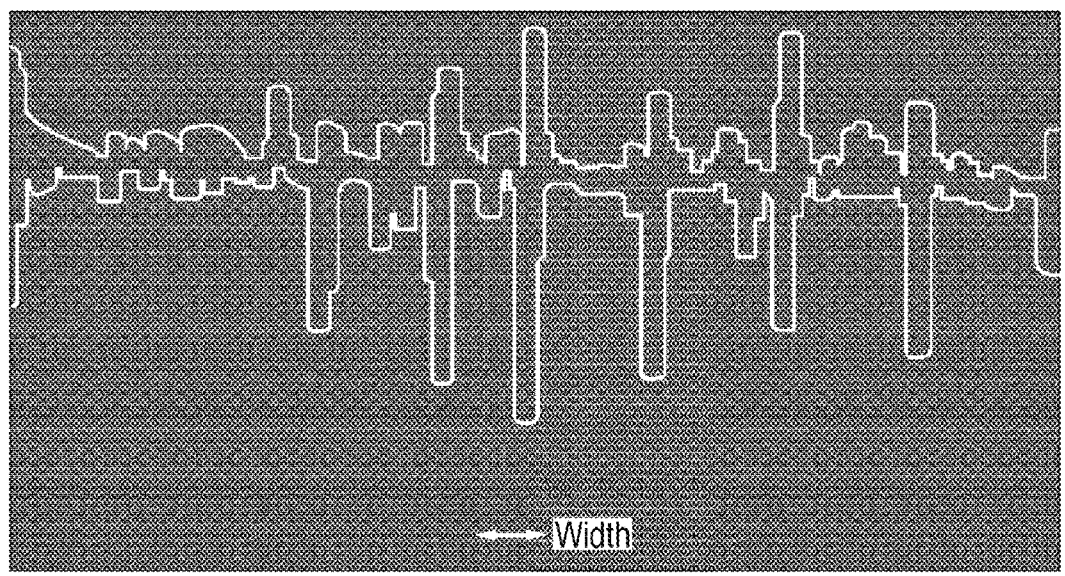
FIG. 5 is a graph showing an enlarged luminance distribution.

FIG. 5 is a graph showing the enlarged luminance distribution 403 or 404. As is apparent from FIG. 5, the luminance distribution has a plurality of portions where the luminance change is large. The portions having large luminance changes indicate granular projections.

The sizes of the projections are almost equal, so luminance widths corresponding to the projections are almost equal. By exploiting the fact that the luminance widths 501 are almost equal, the texture pattern is extracted by the following method. First, the luminance widths 501 (distances) on the lines 401 and 402 are collected.

For the purpose of collection, the average value of all the pixels of an image is calculated, and regions where the luminance value is greatly different from the average value are extracted. Then, the average value of the luminance widths 501 of the extracted regions is calculated. Since the sizes of all projections are almost equal, the average value of the luminance widths 501 becomes almost equal to all the luminance widths corresponding to the texture pattern. Hence, the luminance width 501 almost equal to the average value of the extracted luminance widths 501 can be regarded as the luminance width 501 arising from the texture pattern. The extracted region having the luminance width 501 almost equal to the average value is set to the same value as a neighboring luminance value. As a result, the region having the luminance width 501 is deleted, and the image of the surface of the image sensing target 107 from which the texture pattern is deleted can be obtained.

By this processing, the image of the surface of the image sensing target 107 can be blurred. In addition, a variety of blur methods have been proposed. As another method, for example, the average value of pixels is calculated. According to this method, the average value of pixel values in a region near each pixel of the image of the surface of the image sensing target 107 is calculated first. Then, the target pixel value is replaced with the calculated average value. This processing is executed for all pixels to replace each pixel value with the average value of pixels, obtaining a blurred image. A concrete example of blur processing using the average value will be described below.

Figure 6:
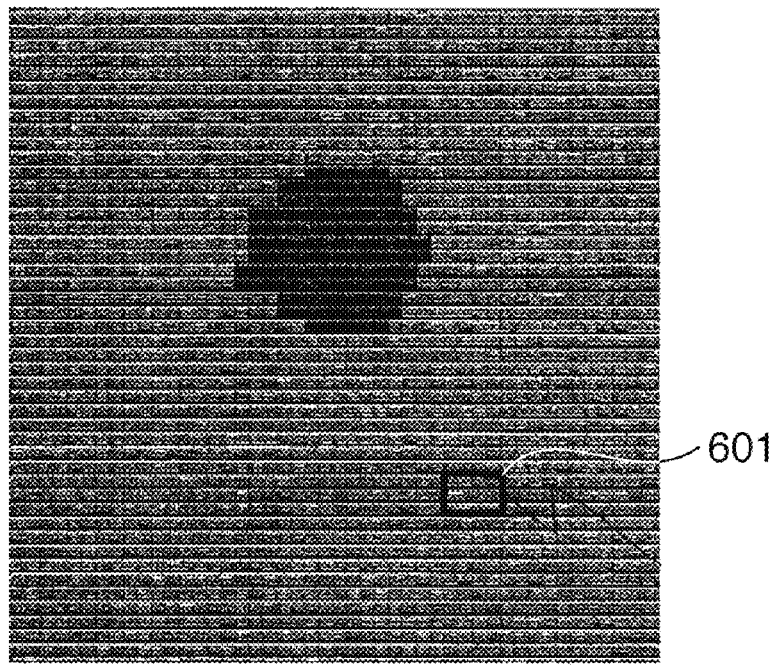
FIG. 6 is a view exemplifying a texture pattern appearing on the surface of an image sensing target.

FIG. 6 exemplifies another texture pattern appearing on the surface of the image sensing target 107. The texture pattern appearing on the surface of the image sensing target 107 shown in FIG. 6 arises from a tile-like rough surface covering the surface of the image sensing target 107. When performing blur processing for the image sensing target 107 in FIG. 6, a region corresponding to the tile size is set. By calculating the average pixel value of each region, proper blur processing can be done. The region corresponding to the tile size is a region set to extract pixels falling in a region near the target pixel.

More specifically, a rectangular region 601 larger than the tile is set. Then, averaging processing is executed in the rectangular region 601 by using, as a center, each of all the pixels of the sensed image. By performing averaging processing using the rectangular region 601 larger than the tile, a sensed image free from the seams between tiles can be attained.

Figure 7:
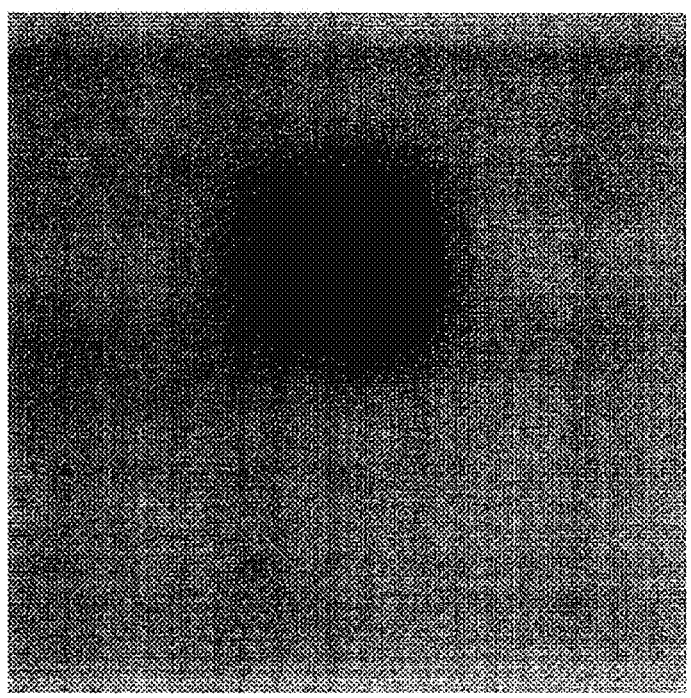
FIG. 7 is a view showing an image obtained by performing blur processing for the image of FIG. 6.

FIG. 7 is a view showing an image obtained by performing blur processing for the image of FIG. 6. FIG. 7 reveals that an image in which a defective portion is enhanced can be obtained by performing blur processing.

Figure 8:
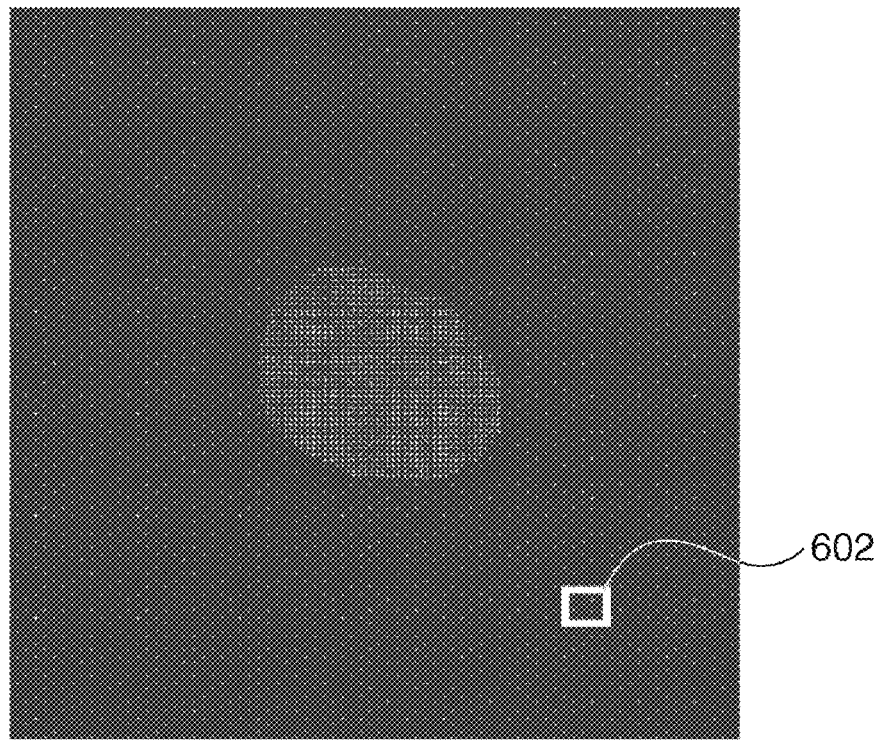
FIG. 8 is a view exemplifying a texture pattern appearing on the surface of an image sensing target.

FIG. 8 exemplifies still another texture pattern appearing on the surface of the image sensing target 107. FIG. 8 shows a state in which a granular pattern is generated on the image sensing target 107.

Figure 9:
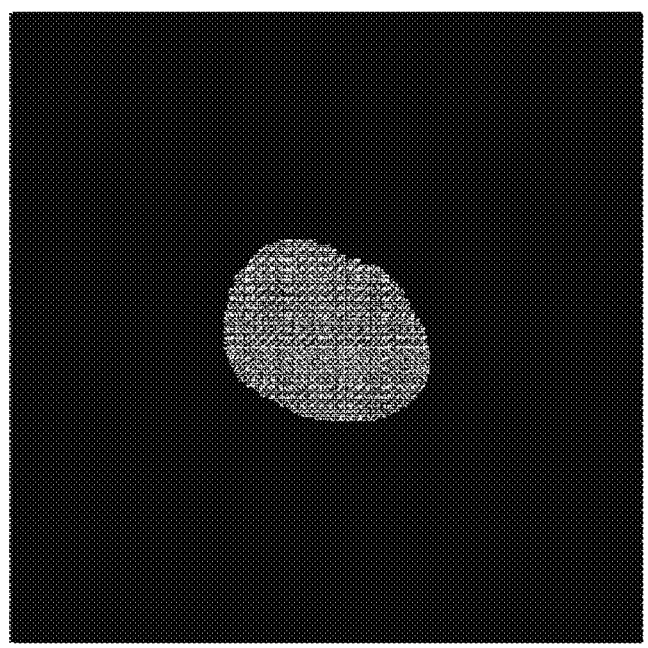
FIG. 9 is a view showing an image obtained by performing blur processing for the image of FIG. 8.

Blur processing can be executed by setting a rectangular region 602 double or more the grain in length and breadth and performing averaging processing, similar to the processing in FIG. 6. FIG. 9 is a view showing an image obtained by performing blur processing for the image of FIG. 8.

A defective portion can be extracted at higher accuracy by executing blur processing corresponding to the surface structure or material of the image sensing target 107, like the above-described processing. As a method of actually performing blur processing, rectangular regions corresponding to predetermined texture patterns may be stored in a storage device in advance. In this case, the user selects a texture pattern, and the control means 105 selects an appropriate rectangular region.

(Step 204) In step 204, the control means 105 functions as a region extraction function and extracts a defective portion region from the image of the surface of the image sensing target 107. By the processing of step 203, the image of the image sensing target 107 is blurred. A boundary is extracted at which the luminance value changes by a preset or more value. Accordingly, the boundary of the defective portion can be extracted without erroneously detecting the texture pattern as a defective portion.

When the size and shape of a defective portion region are known in advance, the defective portion may be extracted without performing the processing of step 203. For example, all the boundaries of regions where the luminance value changes by a preset value or more are extracted from the image sensing target 107. Then, the coincidence between the known size or shape of the defective portion region and each extracted region is calculated. The coincidence is the quantified value of the similarity between the shapes of two regions that is calculated based on the area difference or the like. Various methods have been proposed as the method of calculating the coincidence between region shapes, and a detailed description thereof will be omitted. By the above processing, the coincidence is calculated, and a region having the highest coincidence is set as a defective portion region.

(Step 205) In step 205, the control means 105 calculates the evaluation value of each image acquired in step 202. The evaluation value is a quantified value representing whether image sensing conditions are suitable for detecting a defective portion. The evaluation value is based on the contrast between a defective portion region and the remaining region. Let A1 be the area of the defective portion extracted in step 204 and Q1 be the contrast value in the defective portion region. Also, let A2 be the area of a region other than the defective portion extracted in step 204 and Q2 be the contrast value of the region other than the defective portion region extracted in step 204. Then, an evaluation value L can be given by $$L = A1 \times Q1 / A2 \times Q2$$

For example, if the scratch of the defective portion region appears clearly on the image, the contrast in the defective portion region becomes high and the evaluation value L becomes large. Depending on an acquired image, a defective portion does not or hardly appears. In this case, the area of the defective portion region is small and the evaluation value becomes low.

As the evaluation value L calculated by this processing is larger, image sensing conditions can be regarded to be better for extracting a defective portion.

The equation to calculate the evaluation value L is not limited to the above-described one and is arbitrary as long as the evaluation value L reflects the contrast between the defective portion region and the remaining region.

Depending on the arithmetic processing performance of the visual inspection apparatus, the sum of the absolute values of luminance values in the defective portion region extracted in step 204 may be used more simply as the evaluation value.

(Step 206) In step 206, the control means 105 obtains image sensing conditions suited to visual inspection based on the evaluation value calculated in step 205.

Figure 10:
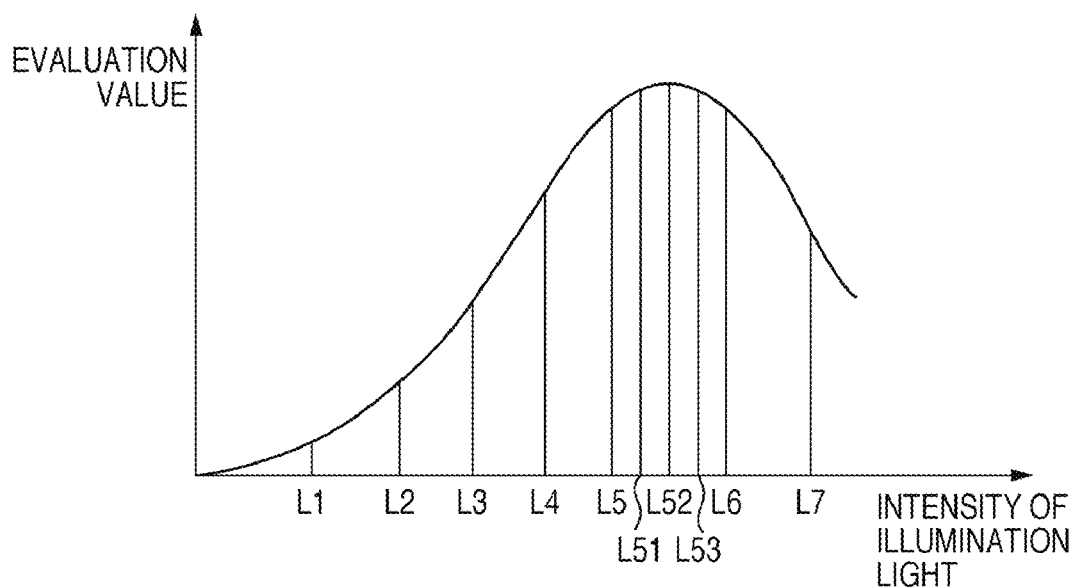
FIG. 10 is a graph showing the correspondence between the intensity of illumination light and the evaluation value.

FIG. 10 is a graph showing the correspondence between the intensity of illumination light serving as one image sensing condition and the evaluation value.

As is apparent from FIG. 10, if the illuminance intensity is low, like L1, the entire image of the image sensing target 107 becomes dark and the contrast between the defective portion and the remaining region becomes low. The poor contrast between the defective portion and the remaining region leads to a small evaluation value.

If the illuminance intensity is too high, like L7, the shade is hardly generated in the image. Further, the illuminance intensity exceeds a luminance range sensible by the image sensing means, decreasing the contrast between the defective portion and the remaining region. An excessively high illumination intensity results in a small evaluation value, too.

In FIG. 10, the evaluation value tends to rise up to the intensity L5 of illumination light and drop from the illumination condition L6. An illumination condition under which the evaluation value maximizes should reside between the illumination conditions L5 and L6. The control means 105 presents, on the display device such as a monitor, the fact that a better visual inspection can be achieved by setting an illumination condition between the illumination conditions L5 and L6. By checking the display, the user who performs a visual inspection can confirm an image sensing condition suited to the visual inspection. In this processing, the control means 105 functions as the first control means for obtaining an image sensing condition at a predetermined time interval. When the user designates to obtain a more accurate image sensing condition, the process returns to step 202 to execute the foregoing processing.

At this time, the control means 105 functions as the second control means for obtaining a more accurate image sensing condition and limits, to the range between the illumination conditions L5 and L6, the range where the image sensing condition is changed, thereby narrowing the image sensing time interval in step 202. At the narrow time interval, the intensity of illumination light having a large evaluation value can be detected at higher accuracy. For example, by calculating evaluation values at L51, L52, and L53 in FIG. 10, the intensity of illumination light at L52 having a larger evaluation value can be detected. In this fashion, the evaluation value is calculated at the first large time interval. After that, the evaluation value is calculated at the second small time interval within the range where the evaluation value changes from the upward trend to the downward trend. The intensity of illumination light having a large evaluation value can be detected quickly. The control means 105 functions as an image sensing condition setting means and sets the image sensing condition obtained by the processing of FIG. 2 as an image sensing condition used when performing a visual inspection.

An inspection can be achieved at higher detection accuracy by the image sensing apparatus in FIG. 1 functioning as a visual inspection apparatus using image sensing conditions set by the processing of FIG. 2.

In the foregoing processing, the intensity of illumination light is mainly used as an image sensing condition. The same processing can also be applied to, for example, the relative positions of the image sensing means 103, image sensing target 107, and illumination means 102.

In the processing of step 206, the image sensing time interval is narrowed based on a user instruction, and then the processes in step 202 and subsequent steps are executed again. Instead, for example, the process may return to step 206 only by a preset count. When the process returns to step 206 only by a preset count, an appropriate image sensing condition can be easily detected without putting a heavy burden on the user.

Second Embodiment

In the first embodiment, the 2D search region 303 is set based on a user instruction using the UI 301 in FIG. 3. In the second embodiment, a 3D search region 303 is set in step 201 of FIG. 2. Processing other than step 201 of FIG. 2 is the same as that in the first embodiment, and a description thereof will not be repeated.

Figure 11:
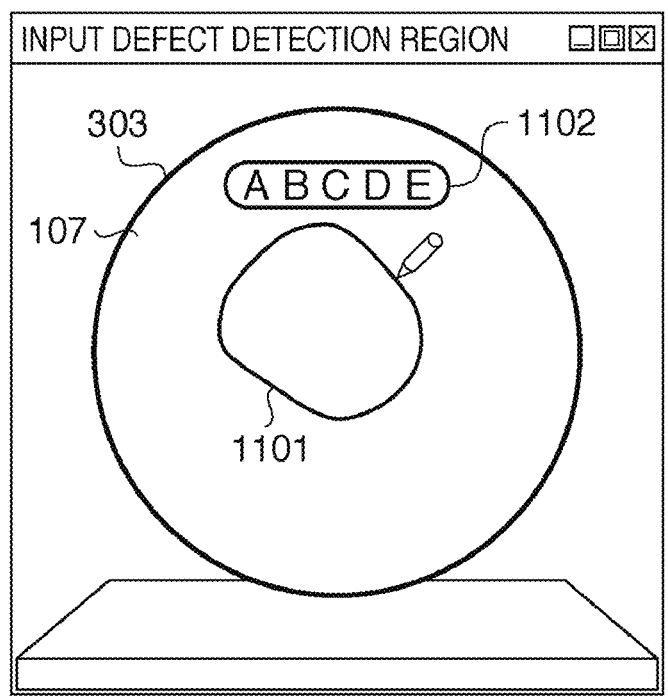
FIG. 11 is a view showing a UI (User Interface) for setting a search region in the second embodiment.

FIG. 11 is a view showing a UI (User Interface) for setting a search region in the second embodiment.

First, the search region 303 is set for an image sensing target 107, similar to the first embodiment. Then, another search region 303 is set for the image sensing target 107 when observed from a direction different from that in FIG. 11.

Figure 12:
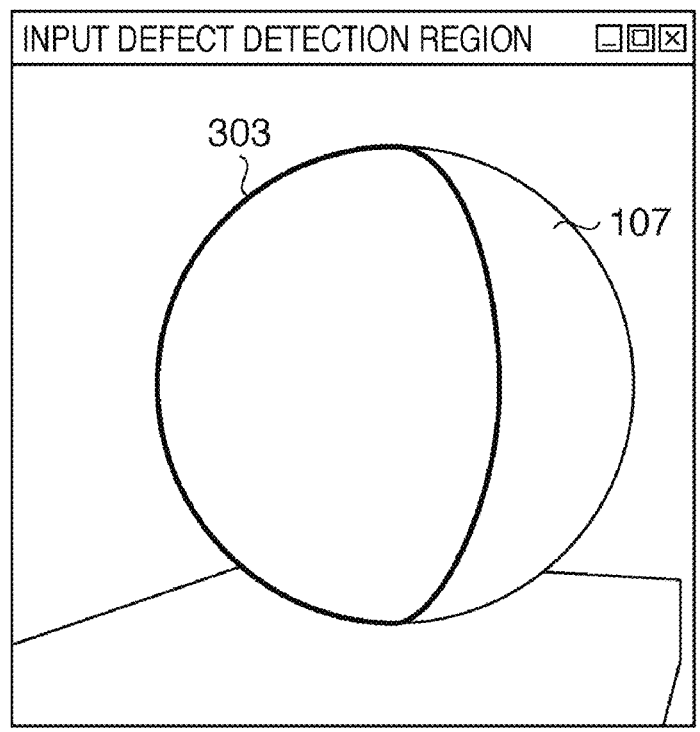
FIG. 12 is a view showing an image sensing target observed from a direction different from that in FIG. 11.
Figure 13:
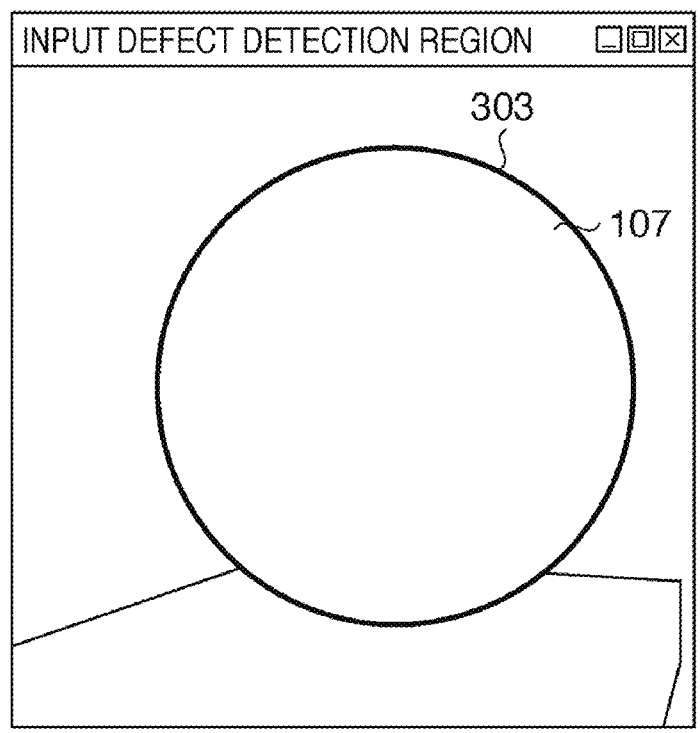
FIG. 13 is a view showing the image sensing target observed from a direction different from that in FIG. 11.

FIGS. 12 and 13 are views showing the image sensing target 107 observed from directions different from that in FIG. 11.

FIG. 12 is a view showing the image sensing target 107 observed from the side. The search region 303 is set to cross the image sensing target 107.

FIG. 13 is a view showing the image sensing target 107 observed from the back. The search region 303 is set to cover the entire region of the image sensing target 107.

By setting a plurality of 2D search regions as described above, a 3D search region can be set. More specifically, a plurality of 2D search regions are set at 3D coordinates. A space in which no 2D search region is set is complemented by the set 2D search regions, thereby setting a search region.

In the first embodiment, the search region 303 is reconfigured to sense an image in various directions. In contrast, the second embodiment can omit reconfiguration processing by setting the 3D search region 303.

Based on a user instruction, an exceptional region 1102 in FIG. 11 may be set, which has a design, logotype, or the like, is apparently not a defective portion region but may be erroneously detected as a defective portion region. The exceptional region 1102 is not referred to in the processing sequence of FIG. 2. By setting the exceptional region 1102, it is not erroneously detected as a defective portion region, increasing the detection accuracy of the defective portion region.

Since the exceptional region 1102 need not be processed, the processing speed can be increased.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-172749, filed Jun. 29, 2007, which is hereby incorporated by reference herein in its entirety.

The invention claimed is:

1. An image sensing apparatus comprising:
    an image sensing unit configured to sense an image sensing target which has a defective portion region;
    an image sensing condition change unit configured to change an image sensing condition while the image sensing unit senses the image sensing target;
    a calculation unit configured to calculate an evaluation value corresponding to the contrast between the defective portion region of the sensed image and a region other than the defective region of the sensed image;
    a first control unit configured to operate the image sensing unit and the calculation unit at a first time interval in parallel with operation of the image sensing condition change unit;
    a second control unit configured to operate the image sensing unit and the calculation unit within a range where the evaluation value obtained by the operation of the first control unit changes from increase to decrease at a second time interval smaller than the first time interval in parallel with operation of the image sensing condition change unit; and
    an image sensing condition setting unit configured to set the image sensing condition based on the evaluation value obtained by the operation of the second control unit.

2. The image sensing apparatus according to claim 1, wherein the image sensing condition includes at least either of an intensity of illumination light by an illumination unit and relative positions of the image sensing unit, the image sensing target, and the illumination unit.

3. The image sensing apparatus according to claim 1, further comprising region extraction unit configured to extract the defective portion region of the image sensing target based on a user instruction.

4. The image sensing apparatus according to claim 1, wherein
    the calculation unit calculates an evaluation value corresponding to a low contrast of the sensed image, and
    the second control unit controls the image sensing condition change unit to change the image sensing condition within a range where the evaluation value obtained by the first control unit changes from decrease to increase, the image sensing unit to sense the image sensing target at every second time interval smaller than the first time interval, and the calculation unit to calculate an evaluation value of the sensed image.

5. An image sensing apparatus comprising:
    an image sensing unit configured to sense an image sensing target to acquire a sensed image;

an enhancement processing unit configured to enhance a defective portion region on the sensed image acquired by the image sensing unit in accordance with a surface structure of the image sensing target; and an image sensing condition setting unit configured to set an image sensing condition of the image sensing unit based on the sensed image in which the defective portion region is enhanced, wherein the enhancement processing unit sets, in accordance with the surface structure of the image sensing target, a neighboring region of a pixel which forms the sensed image, and changes a pixel value of the pixel to an average pixel value in the neighboring region.

6. The image sensing apparatus according to claim 5, further comprising a condition setting unit configured to calculate, as an evaluation value, information on a contrast of the sensed image in which the defective portion region is enhanced, and setting an image sensing condition based on the calculated evaluation value.

7. The image sensing apparatus according to claim 5, wherein the image sensing condition includes at least either of an intensity of illumination light by an illumination unit and relative positions of the image sensing unit, the image sensing target, and the illumination unit.

8. The image sensing apparatus according to claim 5, wherein the surface structure of the image sensing target includes either of a shape and material of a surface of the image sensing target.

9. An image sensing apparatus comprising:

an image sensing unit configured to sense an image sensing target which has a defective portion region;

an image sensing condition change unit configured to change an image sensing condition while the image sensing unit senses the image sensing target;

an enhancement processing unit configured to enhance a defective portion region on the sensed image in accordance with a surface structure of the image sensing target;

a calculation unit configured to calculate an evaluation value corresponding to the contrast between the defective portion region of the sensed image and a region other than the defective portion region of the sensed image;

a first control unit configured to operate the image sensing unit and the calculation unit at a first time interval in parallel with operation of the image sensing condition change unit;

a second control unit configured to operate the image sensing unit and the calculation unit within a range where the evaluation value obtained by the operation of the first control unit changes from increase to decrease at a second time interval smaller than the first time interval in parallel with operation of the image sensing condition change unit; and an image sensing condition setting unit configured to set the image sensing condition based on the evaluation value obtained by the operation of the second control unit.

10. The image sensing apparatus according to any one of claims 1, 2, 3 to 5 or 6 to 8, further comprising visual inspection unit configured to perform a visual inspection of the image sensing target under the image sensing condition set by the image sensing condition setting unit.

11. An image sensing method comprising:

an image sensing step of causing an image sensing unit to sense an image sensing target which has a defective portion region;

an image sensing condition change step of causing an image sensing condition change unit to change an image sensing condition when sensing while the image sensing target is sensed;

a calculation step of causing a calculation unit to calculate an evaluation value corresponding to the contrast between the defective portion region of the sensed image and a region other than the defective portion region of the sensed image;

a first control step of operating the image sensing unit and the calculation unit at a first time interval in parallel with operation of the image sensing condition change unit;

a second control step of operating the image sensing unit and the calculation unit within a range where the evaluation value obtained by the execution of the first control step changes from increase to decrease at a second time interval smaller than the first time interval in parallel with operation of the image sensing condition change unit; and an image sensing condition setting step of setting the image sensing condition based on the evaluation value obtained in the second control step.

12. An image sensing method comprising:

an image sensing step of causing an image sensing unit to sense an image sensing target and acquire a sensed image;

an enhancement processing step of causing an enhancement processing unit to enhance a defective portion region on the sensed image acquired by the image sensing unit in accordance with a surface structure of the image sensing target; and an image sensing condition setting step of causing an image sensing condition setting unit to set an image sensing condition of the image sensing unit based on the sensed image in which the defective portion region is enhanced, wherein, in the enhancement processing step, in accordance with the surface structure of the image sensing target, a neighboring region of a pixel is set which forms the sensed image, and a pixel value of the pixel is changed to an average pixel value in the neighboring region.

13. An image sensing method comprising:

an image sensing step of causing an image sensing unit to sense an image sensing target which has a defective portion region;

an image sensing condition change step of causing an image sensing condition change unit to change an image sensing condition while the image sensing target is sensed;

an enhancement processing step of causing an enhancement processing unit to enhance the defective portion region on the sensed image in accordance with a surface structure of the image sensing target;

a calculation step of causing a calculation unit to calculate an evaluation value corresponding to the contrast between the defective portion region of the sensed image and a region other than the defective portion region of the sensed image;

a first control step of operating the image sensing unit and the calculation unit at a first time interval in parallel with operation of the image sensing condition change unit;

a second control step of operating the image sensing unit and the calculation unit within a range where the evaluation value obtained by the execution of the first control step changes from increase to decrease at a second time interval smaller than the first time interval in parallel with operation of the image sensing condition change unit; and an image sensing condition setting step of setting the image sensing condition based on the evaluation value obtained by the execution of the second control step.

14. A non-transitory computer readable storage medium storing a program that causes a computer to function as an image sensing unit configured to sense an image sensing target which has a defective portion region, an image sensing condition change unit configured to change an image sensing condition while the image sensing unit senses the image sensing target, a calculation unit configured to calculate an evaluation value corresponding to the contrast between the defective portion region of the sensed image and a region other than the defective portion region of the sensed image, a first control unit configured to operate the image sensing condition change unit and the calculation unit at a first time interval in parallel with operation of the image sensing condition change unit, a second control unit configured to operate the image sensing unit and the calculation unit within a range where the evaluation value obtained by the operation of the first control unit changes from increase to decrease at a second time interval smaller than the first time interval in parallel with operation of the image sensing condition change unit, and an image sensing condition setting unit configured to set the image sensing condition based on the evaluation value obtained by the operation of the second control unit.

15. A non-transitory computer readable storage medium storing a program that causes a computer to function as an image sensing apparatus comprising:

an image sensing unit configured to sense an image sensing target to acquire a sensed image;

an enhancement processing unit configured to enhance a defective portion region on the sensed image acquired by the image sensing unit in accordance with a surface structure of the image sensing target; and an image sensing condition setting unit configured to set an image sensing condition of the image sensing unit based on the sensed image in which the defective portion region is enhanced, wherein the enhancement processing unit sets, in accordance with the surface structure of the image sensing target, a neighboring region of a pixel which forms the sensed image, and changes a pixel value of the pixel to an average pixel value in the neighboring region.

16. A non-transitory computer readable storage medium storing a program that causes a computer to function as an image sensing unit configured to sense an image sensing target which has a defective portion region, an image sensing condition change unit configured to change an image sensing condition while the image sensing unit senses the image sensing target, an enhancement processing unit configured to enhance a defective portion region on the sensed image in accordance with a surface structure of the image sensing target, a calculation unit configured to calculate an evaluation value corresponding to the contrast between the defective portion region of the sensed image and a region other than the defective portion region of the sensed image, a first control unit configured to operate the image sensing unit and the calculation unit at a first time interval in parallel with operation of the image sensing condition change unit, a second control unit configured to operate the image sensing unit and the calculation unit within a range where the evaluation value obtained by the operation of the first control unit changes from increase to decrease at a second time interval smaller than the first time interval in parallel with operation of the image sensing condition change unit, and an image sensing condition setting unit configured to set the image sensing condition based on the evaluation value obtained by the operation of the second control unit.

* * * * *